(12) United States Patent
Harvey

(10) Patent No.: US 9,790,445 B1
(45) Date of Patent: *Oct. 17, 2017

(54) HIGH DENSITY DIAMONDOID FUELS FROM RENEWABLE OILS, TRIGLYCERIDES, AND FATTY ACIDS

(71) Applicant: The United States of America as Represented by the Secretary of the Navy, Washington, DC (US)

(72) Inventor: Benjamin G. Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/613,464

(22) Filed: Jun. 5, 2017

Related U.S. Application Data

(60) Division of application No. 15/099,190, filed on Apr. 14, 2016, now Pat. No. 9,738,843, which is a continuation-in-part of application No. 14/311,588, filed on Jun. 23, 2014, now Pat. No. 9,546,332, and (Continued)

(51) Int. Cl.

| C06B 47/00 | (2006.01) |
| D03D 23/00 | (2006.01) |
| D03D 43/00 | (2006.01) |
| C10L 1/08 | (2006.01) |
| C10L 10/12 | (2006.01) |
| C07C 4/06 | (2006.01) |
| C07C 1/207 | (2006.01) |

(52) U.S. Cl.
CPC .............. *C10L 1/08* (2013.01); *C07C 1/2076* (2013.01); *C07C 4/06* (2013.01); *C10L 10/12* (2013.01); *C10L 2200/0469* (2013.01); *C10L 2270/026* (2013.01); *C10L 2270/04* (2013.01); *C10L 2290/06* (2013.01); *C10L 2290/24* (2013.01); *C10L 2290/543* (2013.01)

(58) Field of Classification Search
USPC ...................................... 149/109.6, 1, 109.4
See application file for complete search history.

(56) References Cited

U.S. PATENT DOCUMENTS 3,595,797 A * 7/1971 Haseltine et al. ........ C10M 3/00
                                                          252/73
9,738,843 B1 * 8/2017 Harvey ..................... C10L 1/08
(Continued)

OTHER PUBLICATIONS

Chung, et al. Recent developments in high-energy density liquid hydrocarbon fuels, Energy & Fuels, 1999, 13, 641-649.
(Continued)

*Primary Examiner* — James McDonough
(74) *Attorney, Agent, or Firm* — Charlene A. Haley

(57) ABSTRACT

A method for making high density fuels including, heating a renewable plant oil, triglyceride, or fatty acid with at least one first acid catalyst to generate a first mixture of alkyladamantanes, increasing reaction time or adding at least one second catalysts to a first mixture of alkyladamantanes to produce a second alkyladamantane mixture, separating methyl, ethyl, propyl, and/or butyl adamantanes from a second alkyladamantane mixture to produce a third adamantane mixture to produce fuels.

15 Claims, 1 Drawing Sheet

Related U.S. Application Data a continuation-in-part of application No. 15/297,285, filed on Oct. 19, 2016.

(56) References Cited

U.S. PATENT DOCUMENTS

| | | | | |
|---|---|---|---|---|
| 2009/0177019 A1* | 7/2009 | Saito | ............... | B01J 29/126 585/352 |
| 2015/0011810 A1* | 1/2015 | Harvey | ............... | C10L 1/04 585/22 |

OTHER PUBLICATIONS

Ma, et al. ionic liquids catalytic rearrangment of polycyclic hydrocarbos: a versatile route to alkyl-diamondoid fuels, Amer. Chem. Soc. 2013, 2486-2492.

Badme, et al. Generation of C11-C17 monoalkyladamantane via catalysis of some-O2_containing precursors of Pet. Hydrocarbons. Petroleum Chemisrty 2011, 51, 331-335.

http://msdssearch.dow.com/PublishedLiteratureDOWCOM/dh_052b/0901b8038052b725.pdf?filepath=productsafety/pdfs/noreg/233-00784.pdf&fro.

* cited by examiner

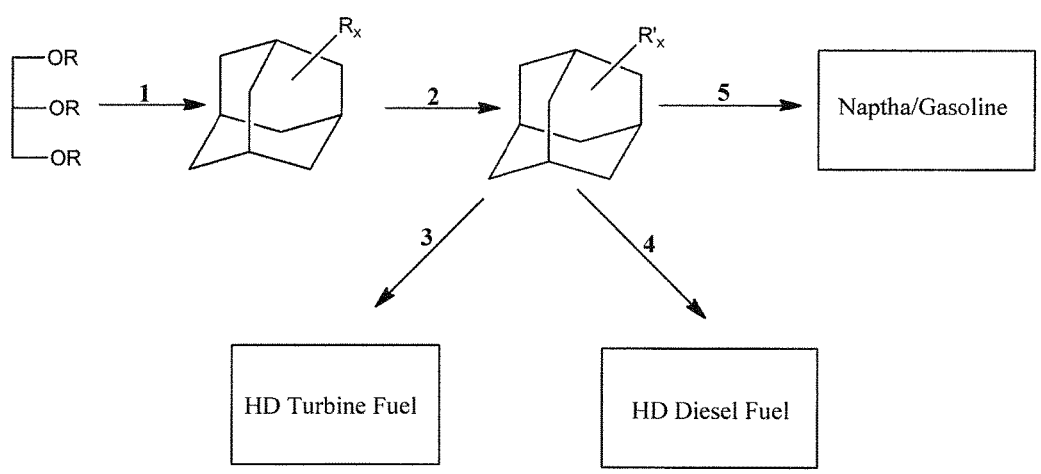

US 9,790,445 B1

HIGH DENSITY DIAMONDOID FUELS FROM RENEWABLE OILS, TRIGLYCERIDES, AND FATTY ACIDS

CROSS-REFERENCE TO RELATED APPLICATIONS

This is a continuation-in-part non-provisional patent application, claiming the benefit of, parent application Ser. No. 14/311,588 filed on Jun. 23, 2014, which claims benefit to provisional patent application Ser. No. 61/840,004 filed on Jun. 27, 2013, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

Embodiments of the invention generally relate to methods for the conversion of vegetable oils into high density fuels with net heats of combustion in excess of 135,000 btu/gal and densities in excess of 0.89 g/mL. The invention further details a method for generating high density fuels suitable for combustion in a diesel engine.

BRIEF DESCRIPTION OF THE DRAWING

The FIGURE is a chemical flow chart showing a conversion of triglycerides to high density diamondoid fuels, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to methods for the conversion of vegetable oils into high density fuels with net heats of combustion in excess of 135,000 btu/gal and densities in excess of 0.89 g/mL. The invention further details a method for generating high density fuels suitable for combustion in a diesel engine.

The fuels described in the disclosure can be prepared from renewable sources and in some cases have net heats of combustion greater than that of JP-10. Further, the fuels can be custom tailored for operation in turbine or diesel engines.

Petroleum derived JP-10 is a high-density fuel used for missile propulsion. It has a density of 0.94 g/mL, a net heat of combustion (NHOC) of 141,500 btu/gal, and excellent low temperature viscosity. These properties make finding a renewable alternative extraordinarily difficult. The current invention describes a process that catalytically converts renewable plant oils into high density diamondoid fuels (FIG. 1). R is an alkyl group having between 1 and 7 carbon atoms. X is an integer from 1 to 4. R' is similarly an alkyl group having between 1 and 7 carbon atoms, but the average molecular weight of AdR'x (Ad=Adamantane) is lower than AdRx. By modifying the oil feedstock, catalyst, and operating conditions; the density, NHOC, low temperature viscosity, and cetane number of the fuels can be optimized. Moreover, the diamondoid scaffold imparts high thermal stability to the fuels.

This invention will allow for the preparation of a variety of high density fuels suitable for both turbine and diesel engines. Particularly in volume limited aircraft, this innovation provides the opportunity to significantly increase range, loiter time, and payload capabilities. As these fuels are derived from renewable plant oils, this process also has the potential to significantly decrease the carbon footprint of the Department of Defense (DoD).

Patent application Ser. No. 14/311,588 filed on Jun. 23, 2014, describes the conversion of sesquiterpenes to diamondoid fuels. Petroleum Chemistry 2011, 51, 331-335 describes conversion of triglycerides to alkyladamantanes. Energy and Fuels 1999, 13, 641-649 describes some properties of petroleum-derived, complex adamantane mixtures.

Embodiments of the invention generally relate to methods for making high density turbine fuels including, heating a renewable plant oil, triglyceride, or fatty acid with at least one first acid catalyst to generate a first mixture of alkyl adamantanes with between 11 and 17 carbon atoms, cracking the first mixture of alkyl adamantanes by continued heating and/or addition of a second catalyst to the first mixture of alkyl adamantanes to produce a second alkyl adamantane mixture with a decreased average molecular weight, fractionally distilling the second alkyl adamantane mixture to produce a third alkyl adamantane mixture enriched in $C_{11}$-$C_{14}$ alkyl adamantanes, and blending the third alkyl adamantane mixture with other petroleum-based or renewable fuels to obtain high density jet/turbine fuels.

Another aspect of the invention generally relates to methods for making high density diesel fuels including, heating a renewable plant oil, triglyceride, or fatty acid with at least one first acid catalyst to generate a first mixture of alkyl adamantanes with between 11 and 17 carbon atoms, separating $C_{14}$-$C_{17}$ alkyl adamantanes from the first alkyl adamantane mixture by fractional distillation to produce a $C_{14}$-$C_{17}$ alkyl adamantane mixture and a $C_{11}$-$C_{14}$ alkyl adamantane mixture, and blending the $C_{14}$-$C_{17}$ alkyl adamantane mixture with other petroleum based or renewable fuels to produce high density diesel fuels.

Still yet another embodiment of the invention generally relates to methods for making high density fuels including, heating a renewable plant oil, triglyceride, or fatty acid with at least one first acid catalyst to generate a first mixture of alkyl adamantanes with between 11 and 17 carbon atoms, cracking the mixture of alkyl adamantanes by continued heating and/or addition of a second catalyst to produce a second alkyl adamantane mixture, separating $C_{11}$-$C_{14}$ alkyl adamantanes from the second alkyl adamantane mixture by fractional distillation to produce a third alkyl adamantane mixture, and isolating low molecular weight cracking products having one to eight carbon atoms from the second alkyl adamantane mixture to produce a naptha stream.

In embodiments, the triglyceride or fatty acid has greater than 11 carbons in the chain. In embodiments, the first and/or second acid catalyst could be heterogeneous acidic catalyst(s). In embodiments, the second catalyst would be more acidic than the first and would lead to more extensive cracking and lower molecular weight adamantanes. In embodiments, the first and/or second acid catalyst is a mesoporous acidic zeolite selected from the group consisting of AlSBA-15 and AlMCM-41. In embodiments, the plant oil, triglyceride, fatty acid, first or second adamantane mixture is heated between about 250° C. and about 450° C. to generate a distribution of alkyl adamantanes. In embodiments, the $C_{14}$-$C_{17}$ adamantane mixture is obtained via fractional distillation and formulated with petroleum-based or renewable hydrocarbons to generate a high density diesel fuel.

In embodiments, the $C_{11}$-$C_{14}$ alkyl adamantane mixture are fractionally distilled to produce a turbine/jet fuel cut or are blended with JP-10, JP-5, JP-8, Jet-A, or renewable jet fuels to produce a final high density fuel. In embodiments, the generation of the first or second alkyl adamantane mixture is conducted in a sealed bomb under an inert atmosphere and high pressure to increase the yield of adamantanes. In embodiments, the generation of the first or second alkyl adamantane mixture is conducted in an open reactor under an inert atmosphere and lower boiling components including $C_{11}$-$C_{14}$ alkyl adamantanes and $C_1$-$C_8$ cracking products are isolated via reactive distillation. In embodiments, the third alkyl adamantane mixture has a density greater than 0.89 g/mL, a volumetric net heat of combustion greater than 135,000 btu/gal, and a cetane number greater than 40. In embodiments, the $C_{14}$-$C_{17}$ alkyl adamantane mixture has a density greater than 0.90 g/mL, a volumetric net heat of combustion greater than 135,000 btu/gal, and a cetane number greater than 40.

1. A renewable plant oil, triglyceride, or fatty acid is heated with an acid catalyst to generate a mixture of alkyladamantanes.
2. Increased reaction time or more acidic catalysts can be used to produce another alkyladamantane distribution.
3. Alkyl adamantanes having between 11 and 14 carbon atoms are separated by fractional distillation and blended with other petroleum-based or renewable fuels to obtain high density jet/turbine fuels.
4. Heavier adamantanes (i.e. C14-C17) are isolated by fractional distillation and blended with other petroleum based or renewable fuels to obtain high density diesel fuels.
5. Light hydrocarbons are collected during the distillation process and are useful as renewable gasoline components.

Methods of Making High Density Fuels (FIG. 1.):
1. Any renewable plant or animal oil/grease containing a significant component of triglycerides or fatty acids can be used. Examples include, but are not limited to, sunflower oil, corn oil, olive oil, linseed oil, castor oil, jatropha oil, etc. Any triglyceride or fatty acid with greater than 11 carbons in the chain can be utilized. Complex mixtures of triglycerides (e.g. waste cooking oils) are also suitable substrates. The acid catalyst is a heterogeneous acidic catalyst. Mesoporous acidic zeolites including AlSBA-15 and AlMCM-41 are particularly well-suited for the reaction. The reaction mixture is heated between ~250 degrees C. and 450 degrees C. (preferably between 300 and 350 degrees C.) to generate a distribution of alkyladamantanes. The distribution is affected by the reaction temperature, the acidity of the catalyst, and the composition of the starting material.
2. The reaction time is selected to produce a preferred distribution of alkyladamantanes. Longer reaction times lead to increased cracking and shorter alkyl chain lengths. To produce primarily a turbine/jet fuel, longer reaction times on the order of ~10 h are used. To produce fuels more suitable for diesel propulsion, shorter reaction times on the order of ~3 h are used. To produce both components in significant quantities an intermediate reaction time is utilized. Along with reaction time, the acidity of the catalyst can be used to optimize the product distribution. More acidic catalysts (in the case of aluminosilicates, higher concentrations of alumina) lead to more cracking which results in greater concentrations of C11-C14 alkyl adamantanes.
3. C11-C14 adamantanes are fractionally distilled to produce a turbine/jet fuel cut. These hydrocarbons can be directly used as a high density turbine fuel, or be blended with JP-10, JP-5, JP-8, Jet-A, or renewable jet fuels to produce a final high density fuel.
4. Heavier adamantanes (C14-C17) are obtained via fractional distillation and can be formulated with petroleum based or renewable hydrocarbons to generate a high density diesel fuel.
5. Light hydrocarbons resulting from the cracking process are collected during the distillation process and are useful as renewable gasoline components.

In embodiments, the reaction can be conducted in a sealed bomb under an inert atmosphere and high pressure to increase the yield of adamantanes. In embodiments, the reaction can be conducted in an open reactor under an inert atmosphere and lower boiling components can be isolated via reactive distillation. In embodiments, the catalyst can be recycled. In embodiments, the process can be conducted in a continuous fashion.

PROPHETIC EXAMPLES

Prophetic examples are for illustration purposes only and not to be used to limit any of the embodiments.

The invention generally relates to processes for the conversion of renewable, bio-derived sesquiterpenes and other isoprenoids to high density diamondoid fuels including alkyl-adamantane fuels where the resulting fuels have net heats of combustion higher than conventional petroleum based fuels. The invention also generally relates to higher terpenes, including diterpenes and triterpenes, and to functionalized isoprenoids, but not limited to terpene alcohols, aldehydes, and epoxides, which can also be converted to high-density diamondoid fuels. High density fuels with improved volumetric net heats of combustion (NHOC) compared to conventional fuels can significantly increase the range, loiter time, or payload of a variety of platforms including missiles, aircraft, and unmanned systems. Embodiments of the invention describe a process for the conversion of renewable, bio-derived sesquiterpenes to high density diamondoid fuels. The resulting fuels have net heats of combustion higher than conventional petroleum based fuels.

Diamondoids are polycyclic hydrocarbons. Alkyl diamondoids (for example, alkyladamantanes) are very attractive for use as high-density fuels due to their high densities, low freezing points, and low viscosities. Renewable fuels based on acyclic hydrocarbons typically have densities that are below the specifications for common aviation and military fuels including Jet-A, JP-5, JP-8, and F-76. The resulting decrease in volumetric net heat of combustion limits the range, loiter time, and payload of both commercial and military aircraft, as well as missiles, UAVs, and other platforms. Embodiments of the invention describe methods to generate fuels with properties that meet or exceed those of conventional petroleum derived fuels. Embodiments of the invention describe methods to generate dense, alkylated, multi-cyclic diamondoid fuels from bio-derived sesquiterpenes. This process can be conducted with both heterogeneous and homogenous catalysts. The resulting multi-cyclic structures have densities and volumetric net heats of combustion that are significantly higher than state-of-the-art fuels, while maintaining low viscosities which allow for use at low temperature/high altitude. Moreover, bio-derived sesquiterpenes can be produced from renewable biomass sources. Use of these fuels will decrease Navy dependence on fossil fuels and will also reduce net carbon emissions.

A general chemical scheme for converting isoprenoids to diamondoid fuel is using sesquiterpenes as an example. The chemistry is as follows. The sesquiterpenes are hydrogenated to generate saturated hydrocarbons. When the isoprenoids are hydrogenated tricyclic sesquiterpenes, they will have the formula $C_{15}H_{26}$; hydrogenated bicyclic sesquiterpenes will have the formula $C_{15}H_{28}$; hydrogenated monocyclics will have the formula $C_{15}H_{30}$ and hydrogenated acyclic sesquiterpenes will have the formula $C_{15}H_{32}$. The saturated hydrocarbons are then isomerized with an acidic catalyst to produce a diamondoid fuel. The diamondoid fuel is purified, and/or various cuts are removed for specific applications, by distillation. The distilled fuel is used directly or is formulated/blended for specific fuel applications. For example, the alkyl-adamantane fuels of the invention may be blended with, but not limited to, Jet A, JP-10, JP-5, F-76, or other renewable fuels including fuels derived from biobutene, biohexene, etc. The alkyl-adamantane fuels that are embodiments of the invention will normally be a mixture of various alkyl-adamantanes and sesquiterpanes. The amount of sesquiterpane may be in the range of about 1% to 90% of the alkyl-adamantine fuel.

Sesquiterpenes are isolated from a renewable source. Sesquiterpenes can be generated by a biosynthetic process that utilizes sugar, biomass sugars, $CO_2$, or CO as a carbon source. Synthetic sesquiterpenes can be used and prepared directly from isoprene or from a reaction between terpenes and isoprene. Alternatively, sesquiterpenes can be extracted from plants using processes that include steam distillation and solvent extraction. Sesquiterpenes can be acyclic. Sesquiterpenes can be mono-cyclic and/or polycyclic hydrocarbons. Cyclic sesquiterpenes can be generated from acyclic sesquiterpenes.

Higher terpenes including diterpenes and triterpenes, can be thermally cracked to form sesquiterpenes. Examples of bio-derived sequiterpenes that are feedstocks embodied in the invention are, but not limited to, farnesene, cadinene, selinene, humulene, copaene, cloven, alpha-neoclovene, longifolene, zizaene, thujopsene, other tricyclic sesquiterpenes, caryophyllene, isomerized caryophyllene mixtures, other bicyclic sesquiterpenes, monocyclic sesquiterpenes including bisabolene, and acyclic sesquiterpenes including farnesene. Bio-derived cyclopentadiene dimers and higher oligomers of bio-derived cyclopentadienes are also disclosed which includes alkylated versions (i.e. tetrahydrodimethyldicyclopentadiene) which we have shown can be generated from linalool, myrcene, and some sesquiterpenes.

The following are publications related to topics of the invention. The basic properties of petroleum-derived diamondoid-type fuels are described in: Chung, H. S.; Chen, C. S. H.; Kremer, R. A.; Boulton, J. R.; Burdette, G. W. Energy Fuels 1999, 13, 641-649. A recent paper has described the conversion of functionalized, hydrogenated cyclopentadienes to diamondoid fuels with ionic liquids: Ma, T.; Feng, R.; Zou, J-J.; Zhang, X.; Wang, Li Industrial and Engineering Chemistry Research 2013, 52, 2486-2492.

Isoprenoid feedstocks, including sesquiterpenes, are hydrogenated to generate saturated hydrocarbons. The hydrogenations can be conducted with either homogenous or heterogeneous catalysts under a hydrogen atmosphere. Hydrogenation catalysts based on nickel, palladium, platinum, ruthenium, and copper are suitable for the reduction. This can typically be conducted without a solvent. Hydrogenations may be conducted with or without a solvent. In some embodiments, addition of a polar solvent increases the reaction rate and allows for the use of milder conditions.

The saturated hydrocarbons are isomerized with acidic catalysts, including a strong Lewis acid or Bronsted acid. Examples of suitable Lewis acid catalysts include $AlCl_3$ and ionic liquids derived from or including $AlCl_3$. Heterogenous Lewis acid catalysts, mesoporous aluminosilicates (e.g. AlMCM-41), and amorphous aluminosilicates, can also be used. Lewis acidic ionic liquids and fluorinated sulfonic acids (heterogeneous and homogenous) are also suitable acidic catalysts for the isomerization.

When heterogeneous catalysts are used in a liquid-phase reaction, the hydrocarbon mixture may be separated by filtration, centrifugation, decantation and/or purified by distillation. In the case of homogenous catalysis, the catalyst may be quenched and the hydrocarbon may be separated by extraction and/or purified by distillation.

Purified alkyl-adamantane fuels may be used directly as high-density fuels or formulated with various conventional or renewable fuels to generate full-performance jet and diesel fuels.

The method shows a general method for converting an isoprenoid and/or functionalized isoprenoid feedstock to an alkyl-adamantane fuel. A first mixture is produced by hydrogenating the feedstock from about 1 to 48 hours with hydrogen gas at pressures ranging from about 1 atm to about 50 atm using a hydrogenation catalyst at temperatures ranging from about 10° to 200° C. An optional polar solvent may be used in the hydrogenation reactor or hydrogenation reaction zone. The first mixture may optionally be distilled to isolate hydrogenated fuel products, including a sesquiterpane. The first mixture is isomerized producing a second mixture. The isomerizing is carried out from about 0.3 to 48 hours using an acidic catalyst at pressures ranging from about 1 atm to about 10 atm at temperatures ranging from about 15° C. to 350° C. The isomerized second mixture is distilled to produce an alkyl-adamantane fuel, which is a mixture of alkyl-adamantanes and isomerized sesquiterpanes, or the second mixture is distilled to produce specific aklyadamantanes and/or specific isomerized sesquiterpanes.

Lewis acids, including acidic ionic liquids, are used to isomerize hydrogenated polycyclic hydrocarbons, including endotetrahydrodicyclopentadiene (endo-THDCPD) to exo-THDCPD, which is the major component of the synthetic fuel called JP-10. Furthermore, both endo- and exo-THD-CPD can be converted to adamantane, the simplest diamondoid, via skeletal rearrangement (isomerization) using aluminum trichloride ($AlCl_3$) as the Lewis acid. The molar fraction of $AlCl_3$ in the ionic liquid determines the acidity of the solvent. Increasing the temperature of the reaction increases the reaction rate and can affect the percent conversion, selectivity, and ratios of various products obtained. A reasonable temperature range for the reaction is from 30° to 120° C. The fact that ionic liquids phase separate from nonpolar hydrocarbons make ionic-liquid-based methods suitable for continuous flow reaction systems.

A continuous-flow process for producing alkyl-adamantane fuel is an embodiment of the invention. The continuous-flow method uses an isoprenoid and/or substituted isoprenoid feedstock, which may include sesquiterpenes. The feedstock is hydrogenated with hydrogen gas using a heterogeneous hydrogenation catalyst to produce a first product stream, which is then isomerized using a heterogeneous acidic catalyst to produce a second product stream. The second product stream is distilled to produce an alkyl-adamantane fuel. The catalysts of the continuous-flow method are supported on fixed beds located in the respective zones. An optional polar solvent may be used, and is fed into the hydrogenating and isomerizing zone. The first product stream is produced by hydrogenating the feedstock having a residence time in the hydrogenation zone from about 0.5 to 48 hours with hydrogen gas at pressures ranging from about 1 atm to about 50 atm at temperatures ranging from about 10° C. to 200° C. The first product stream enters the isomerizing zone. The residence time in the isomerizing zone is about 0.2 to 48 hours at pressures ranging from about 1 atm to about 10 atm and at temperatures ranging from about 15° C. to 350° C. The second product stream exiting the isomerizing zone is distilled to produce an alkyl-adamantane fuel. When an ionic liquid is used, since it is insoluble in the nonpolar hydrocarbon products formed, it may be isolated from the fuel products and recycled back to the isomerizing zone. Optionally, a solid-state crosslinked ionic liquid-like material may be attached to a fixed bed in the isomerizing zone.

Example 1 n-Butyl-1-adamantaneketone 20 g of 1-adamantane carboxylic acid was dissolved in 250 mL THF and then cooled to −20° C. and while cold 93 mL 2.5 M n-BuLi (2.1 equiv) was added slowly dropwise over 1 h. Solids precipitated during this time and then the mixture was stirred at rt overnight. A standard workup generated 20.8 g crude oil. The product was further purified by distillation under reduced pressure. $^1$H(CDCl$_3$): 2.44 (t, J=7.1 Hz, 2H), 2.04 (m, 3H), 1.9-1.63 (m, 12H), 1.59-1.43 (m, 2H), 1.36-1.21 (m, 2H), 0.90 (t, J=7.7 Hz, 3H); 13C (CDCl3): 215.84, 46.45, 38.39, 36.78, 35.76, 28.16, 25.98, 22.62, 14.10. Analysis calcd for $C_{15}H_{24}O$: C, 81.76; H, 10.98. Found: C, 81.71; H, 11.00.

1-Pentyladamantane 2.3 g of n-butyl-1-adamantane ketone, 5 g hydrazine hydrate, 20 mL of diethylene glycol, and 5.6 g KOH were heated to 220° C. for 1 h, brought down to 180° C. for 3 h and then left overnight at 130° C. After a standard workup, this procedure gave 2.43 g of crude product (92%). Reduced pressure distillation gave the compound as a colorless liquid. When the reaction was conducted at ten times the scale, a yield of 97% was obtained. The product doesn't freeze when stored at −30° C. $^1$H(CDCl$_3$): 1.93 (m, 3H), 1.79-1.52 (m, 6H), 1.49-1.43 (m, 6H), 1.37-1.17 (m, 6H), 1.07-0.97 (m, 2H), 0.89 (t, J=7.2 Hz, 3H); 13C(CDCl3): 45.03, 42.82, 37.60, 33.17, 32.48, 29.08, 22.98, 22.29, 14.36. Analysis calcd for $C_{15}H_{26}$: C, 87.3; H, 12.7. Found: C, 87.14; H, 12.75.

Example 2

1-Pentyl adamantane, as an example of an alkyl-adamantane fuel, an embodiment of the invention, has a density of 0.946 g/mL, and a net heat of combustion (NHOC), measured by bomb calorimetry, of 145,997 btu/gal (relative standard deviation of 1.3%). Updated values for 1-pentyl adamantine are: density: 0.9148 g/mL, NHOC=139898 btu/gal.

Example 3

Typical hydrogenation conditions for sesquiterpenes. Hydrogenation of sesquiterpenes including β-caryophyllene, valencene, and premnaspirodiene was conducted in a Parr shaker without the addition of solvent at room temperature and with an overpressure of 40-50 psi of hydrogen. Either 1 g of 10% Pd/C or 0.1 g of $PtO_2$ was used for every 100 g of sesquiterpene. The bomb was shaken until uptake of hydrogen ceased. The hydrogenation of valencene and premnaspirodiene was complete within two hours, while caryophyllene typically required up to 48 hours to fully react. After hydrogenation was complete, the black reaction mixtures were then filtered through a celite pad. Valencane, premnaspirodiane, and caryophyllane were used directly without further purification or were vacuum distilled (85-110° C., 1 Torr) through a 10 in Vigreux column to isolate the hydrogenated sesquiterpenes as colorless oils.

Example 4

. Hydrogenation of Longifolane: 100 mL of longifolene, 30 mL of glacial acetic acid, and 0.1 g of PtO2 were added to a glass bomb. The bomb was placed under 45 psi hydrogen and shaken at room temperature for two h. The acetic acid was removed in a separatory funnel and the longifolane was washed with water (2×20 mL) and a 5% sodium carbonate solution. The longifolane was then purified by vacuum distillation.

Example 5

Hydrogenated sesquiterpanes are combined with an acid catalyst. The catalyst loading, reaction time, and temperature are dependent on the catalyst type. Some general reaction conditions are listed in Table 1. All reactions are conducted under an inert atmosphere and products were purified by either physical separation (heterogeneous catalysts) or quenching/extraction (homogenous catalysts) followed by isolation of either diamondoids or diamondoid/isomerized sesquiterpane mixtures by fractional distillation.

TABLE 1

Common reaction conditions for isomerization of sesquiterpanes to diamondoid fuels

| Catalyst | Temp (° C.) | Time |
|---|---|---|
| AlCl$_3$ | 150-200 | 2-4 h |
| Acidic ionic liquid | 80-120 | 10 min-several h |
| Heterogeneous catalyst | up to 350 °C. | 1-5 h |

Prophetic examples are for illustration purposes only and not to be used to limit any of the embodiments. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Embodiments of the invention generally relate to methods for synthesizing first alkyl-adamantane fuel including, providing a first isoprenoid and/or functionalized isoprenoid feedstock, producing first mixture by hydrogenating the first feedstock with hydrogen gas using at least one first hydrogenation catalyst, producing a second mixture by isomerizing the first mixture from about 0.3 hours to about 48 hours using a first acidic catalyst, and distilling the second mixture to produce the first alkyl-adamantane fuel. Another aspect of the invention generally relates to continuous-flow methods for synthesizing second alkyl-adamantane fuel including, providing second isoprenoid and/or functionalized isoprenoid feedstock, hydrogenating the second feedstock with hydrogen gas using second hydrogenation catalyst to produce first product stream, isomerizing the first product stream using second acidic catalyst to produce second product stream, and distilling the second product stream to produce the second alkyl-adamantane fuel.

In embodiments, in producing the first mixture the hydrogenation catalyst further includes at least one transition-metal selected from the group consisting of, but not limited to, nickel, palladium, platinum, ruthenium, and copper. In embodiments, in producing the first mixture, the hydrogenating further includes adding at least one polar solvent selected from the group consisting of, but not limited to, ethyl acetate, other organic ester, acetic acid, other organic acid, methanol, ethanol, butanol, THF, dioxane, and other alcohols. In embodiments, the producing the first mixture further includes distilling the first mixture to produce at least one sesquiterpane. In embodiments, the homogeneous acidic catalyst is selected from the group consisting of, but not limited to, $AlCl_3$, $FeCl_3$, $TiCl_4$, $ZnCl_2$, $SbF_5$, $BF_3$, Lewis acids based on Ti, V, Cr, Mn, Fe, Co, Ni, Cu, Zn, Al, B, Sn, Sb in various oxidation states, and other homogeneous Lewis-acid compounds.

In embodiments, the producing the second mixture by isomerizing further includes adding at least one ionic liquid selected from the group consisting of, but not limited to, pyridinium ionic liquid, imidazolium ionic liquid, acidic ionic liquid, acidic chloroaluminate ionic liquid, clay-supported chloroaluminate ionic liquid, [1-butyl-3-methylimidazolium][bis(trifluoromethylsulfonyl imide)], [1-butyl-3-methylimidazolium][tricyanomethanide], [tri(butyl)(tridecyl)phosphonium][bis(trifluoro methylsulfonyl imide)], triethylammonium chloroaluminate, [1-butyl-3-methylpyridinium]chloroaluminate, and [1-butyl-3-methylimidazolium]chloroaluminate. In embodiments, the acidic catalyst is a heterogeneous Lewis-acid selected from at least one of the group consisting of, but not limited to, $AlCl_3$, $FeCl_3$, $TiCl_4$, $ZnCl_2$, $SbF_5$, $BF_3$, Lewis acids based on Ti, V, Cr, Mn, Fe, Co, Ni, Cu, Zn, Al, B, Sn, Sb in various oxidation states, and other Lewis-acid compound, and where the heterogeneous acidic catalyst is supported on at least one solid material selected from the group consisting of, but not limited to, zeolite, aluminosilicate, alumina, zirconia, titania, silica, and clay, other acidic metal oxide, crosslinked sulfonated polystyrene, other macroreticular resin, other polymer, crosslinked ionic liquid, crosslinked poly(ionic liquid), and crosslinked ionic liquid gel.

In embodiments, the producing the first mixture by hydrogenating the first feedstock is from about 1 hour to 48 hours with hydrogen gas at pressures ranging from about 1 atm to about 50 atm using the first hydrogenation catalyst at temperatures ranging from about 10° C. to 200° C. and where the producing the second mixture by isomerizing the first mixture is from about 0.3 hour to about 48 hours using the first acidic catalyst at pressures ranging from about 1 atm to about 10 atm at temperatures ranging from about 15° C. to about 350° C. In embodiments, the first alkyl-adamantane fuel produced by the methods herein are included in a blended fuel including, but not limited to, Jet A, JP-10, JP-5, F-76, butene oligomer fuels, and hexene oligomer fuels. In embodiments, the hydrogenating the second feedstock with the second hydrogenation catalyst is conducted with a heterogeneous second hydrogenation catalyst supported on a fixed bed.

In embodiments, the hydrogenating further includes adding at least one polar solvent selected from the group consisting of, but not limited to, ethyl acetate, other organic ester, acetic acid, other organic acid, methanol, ethanol, butanol, and other alcohols. In embodiments, the isomerizing the first product stream of the second acidic catalyst is a heterogeneous second Lewis acid supported on a fixed bed. In embodiments, the first alkyl-adamantane fuel is produced by the methods herein is a blended fuel including Jet A, JP-10, JP-5, F-76, butene oligomers, and hexene oligomers. In other embodiments, the second alkyl-adamantane fuel is produced by the methods herein and is blended with fuels including Jet A, JP-10, JP-5, F-76, biobutene, and biohexene.

In embodiments, the blended fuel has a density of at least 0.90 g/mL and a NHOC of at least 135,000 Btu/gal. In embodiments, the fuel has a cetane number ranging from about 30 to about 42. In embodiments, the blended fuel has a cetane number ranging from about 42 to about 50 and has from about 1% to about 70% of the alkyl-adamantane fuel.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making high density diesel fuels, comprising:
heating a renewable plant oil, triglyceride, or fatty acid with at least one first acid catalyst to generate a first mixture of alkyl adamantanes with between 11 and 17 carbon atoms;
separating $C_{14}$-$C_{17}$ alkyl adamantanes from said first alkyl adamantane mixture by fractional distillation to produce a $C_{14}$-$C_{17}$ alkyl adamantane mixture and a $C_{11}$-$C_{14}$ alkyl adamantane mixture; and blending said $C_{14}$-$C_{17}$ alkyl adamantane mixture with other petroleum based or renewable fuels to produce high density diesel fuels.

2. The method according to claim 1, wherein said triglyceride or fatty acid has greater than 11 carbons in the chain.

3. The method according to claim 1, wherein said first and/or second acid catalyst is a heterogeneous acidic catalyst.

4. The method according to claim 1, wherein said first and/or second acid catalyst is a mesoporous acidic zeolite selected from the group consisting of AlSBA-15 and AlMCM-41.

5. The method according to claim 1, wherein said plant oil, triglyceride, or fatty acid is heated between about 250° C. and about 450° C. to generate a distribution of alkyl adamantanes.

6. The method according to claim 1, wherein said $C_{11}$-$C_{14}$ alkyl adamantane mixture is used as a turbine/jet fuel or blended with JP-10, JP-5, JP-8, Jet-A, or renewable jet fuels to produce a final high density fuel.

7. A method for making high density fuels, comprising:
heating a renewable plant oil, triglyceride, or fatty acid with at least one first acid catalyst to generate a first mixture of alkyl adamantanes with between 11 and 17 carbon atoms;
cracking the mixture of alkyl adamantanes by continued heating and/or addition of a second catalyst to produce a second alkyl adamantane mixture;
fractionally distilling said second alkyl adamantane mixture to produce a third alkyl adamantane mixture enriched in $C_{11}$-$C_{14}$ alkyl adamantanes; and
isolating low molecular weight cracking products having one to eight carbon atoms from said second alkyl adamantane mixture to produce a naptha stream.

8. The method according to claim 7, wherein said triglyceride or fatty acid has greater than 11 carbons in the chain.

9. The method according to claim 7, wherein said first and/or second acid catalyst is a heterogeneous acidic catalyst.

10. The method according to claim 7, wherein said first and/or second acid catalyst is a mesoporous acidic zeolite selected from the group consisting of AlSBA-15 and AlMCM-41.

11. The method according to claim 7, wherein said first and/or second alkyl adamantane mixture is heated between about 250° C. and about 450° C. to generate a distribution of alkyl adamantanes.

12. The method according to claim 7, wherein said generation of said first or second alkyl adamantane mixture is conducted in a sealed bomb under an inert atmosphere and high pressure to increase the yield of adamantanes.

13. The method according to claim 7, wherein said generation of said first or second alkyl adamantane mixture is conducted in an open reactor under an inert atmosphere and lower boiling components including $C_{11}$-$C_{14}$ alkyl adamantanes and $C_1$-$C_8$ cracking products are isolated via reactive distillation.

14. The method according to claim 1, wherein said $C_{14}$-$C_{17}$ alkyl adamantane mixture has a density greater than 0.89 g/mL, a volumetric net heat of combustion greater than 135,000 Btu/gal, and a cetane number greater than 40.

15. The method according to claim 7, wherein said $C_{14}$-$C_{17}$ alkyl adamantane mixture has a density greater than 0.89 g/mL, a volumetric net heat of combustion greater than 135,000 Btu/gal, and a cetane number greater than 40.

* * * * *